United States Patent
Richards

(10) Patent No.: US 8,946,251 B2
(45) Date of Patent: *Feb. 3, 2015

(54) METHOD OF TREATING THERMOREGULATORY DYSFUNCTION WITH PAROXETINE

(71) Applicant: Noven Therapeutics, LLC, Miami, FL (US)

(72) Inventor: Patricia Allison Tewes Richards, Scarsdale, NY (US)

(73) Assignee: Noven Therapeutics, LLC, Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/157,992

(22) Filed: Jan. 17, 2014

(65) Prior Publication Data

US 2014/0235674 A1 Aug. 21, 2014

Related U.S. Application Data

(63) Continuation of application No. 12/292,960, filed on Dec. 1, 2008, now Pat. No. 8,658,663, which is a continuation of application No. 11/499,586, filed on Aug. 4, 2006, now abandoned.

(51) Int. Cl.
*A61K 31/435* (2006.01)
*A61K 31/4525* (2006.01)

(52) U.S. Cl.
CPC .................................. *A61K 31/4525* (2013.01)
USPC ............................ 514/277; 514/183; 514/463

(58) Field of Classification Search
CPC .. C07D 317/06; C07D 211/22; C07D 405/12; A61K 31/4525
See application file for complete search history.

(56) References Cited

U.S. PATENT DOCUMENTS

| | | |
|---|---|---|
| 4,007,196 A | 2/1977 | Christensen et al. |
| 4,721,723 A | 1/1988 | Barnes et al. |
| 4,861,893 A | 8/1989 | Borrett |
| 5,039,803 A | 8/1991 | Smith et al. |
| 5,470,846 A | 11/1995 | Sandyk |
| 5,672,612 A | 9/1997 | Rosen et al. |
| 5,872,132 A | 2/1999 | Ward et al. |
| 5,900,423 A | 5/1999 | Ward et al. |
| 5,955,475 A | 9/1999 | Krape et al. |
| 5,985,322 A | 11/1999 | Andersen et al. |
| 6,063,927 A | 5/2000 | Craig et al. |
| 6,080,759 A | 6/2000 | Ward et al. |
| 6,113,944 A | 9/2000 | Pathak et al. |
| 6,133,277 A | 10/2000 | Wigernick et al. |
| 6,172,105 B1 | 1/2001 | Evenden et al. |
| 6,172,233 B1 | 1/2001 | Ward |
| 6,326,496 B1 | 12/2001 | Brennan |
| 6,369,051 B1 | 4/2002 | Jenkins |
| 6,433,179 B1 | 8/2002 | Wang et al. |
| 6,436,956 B1 | 8/2002 | Murthy et al. |
| 6,440,459 B1 | 8/2002 | Stmpa Diex Del Corral et al. |
| 6,498,184 B2 | 12/2002 | Berendsen |
| 6,541,637 B1 | 4/2003 | Okatake et al. |
| 6,645,523 B2 | 11/2003 | Lemmens et al. |
| 6,660,298 B1 | 12/2003 | Rosen et al. |
| 6,686,473 B2 | 2/2004 | Lemmens et al. |
| 6,699,882 B2 | 3/2004 | Craig et al. |
| 6,716,985 B2 | 4/2004 | Jacewicz et al. |
| 6,881,845 B2 | 4/2005 | Fouget et al. |
| 6,900,327 B2 | 5/2005 | Benneker et al. |
| 6,956,121 B2 | 10/2005 | Pilarski et al. |
| 6,987,124 B2 | 1/2006 | Berendsen |
| 8,658,663 B2 | 2/2014 | Richards |
| 2001/0023253 A1 | 9/2001 | Craig et al. |
| 2002/0035130 A1 | 3/2002 | Craig et al. |
| 2002/0090394 A1 | 7/2002 | Leonard et al. |
| 2002/0193406 A1 | 12/2002 | Craig et al. |
| 2004/0086559 A1 | 5/2004 | Peters et al. |
| 2004/0092519 A1 | 5/2004 | Hassan |
| 2004/0130987 A1 | 7/2004 | Hung et al. |
| 2004/0143120 A1 | 7/2004 | Jacewicz et al. |
| 2004/0152710 A1 | 8/2004 | Deecher et al. |
| 2006/0020014 A1 | 1/2006 | Abou-Gharbia et al. |
| 2006/0020015 A1 | 1/2006 | Abou-Gharbia et al. |
| 2006/0100263 A1 | 5/2006 | Basile et al. |
| 2008/0033050 A1 | 2/2008 | Richards |

FOREIGN PATENT DOCUMENTS

| | | |
|---|---|---|
| WO | WO 96/03710 | 10/1996 |
| WO | WO 99/44601 | 9/1999 |

(Continued)

OTHER PUBLICATIONS

Cheema, Deepti, "Non-hormonal therapy of post menopausal vasomotor symptoms: a structured evidence-based review", Arch Gynecol Obstet, vol. 276, pp. 463-469, 2007.

(Continued)

*Primary Examiner* — Renee Claytor
*Assistant Examiner* — Shobha Kantamneni
(74) *Attorney, Agent, or Firm* — Foley & Lardner LLP

(57) ABSTRACT

The present invention relates to a method for treating a patient suffering from a thermoregulatory dysfunction, especially hot flashes and flushes associated with hormonal changes due to naturally occurring menopause (whether male or female) or due to chemically or surgically induced menopause. The method is also applicable to treating the hot flashes, hot flushes, or night sweats associated with disease states that disrupt normal hormonal regulation of body temperature.

12 Claims, No Drawings

(56) References Cited

FOREIGN PATENT DOCUMENTS

| WO | WO 99/47519 | 9/1999 |
|---|---|---|
| WO | WO 99/56751 | 11/1999 |
| WO | WO 00/78291 | 12/2000 |
| WO | WO 2007/043057 | 4/2007 |

OTHER PUBLICATIONS

Stearns, MD et al.; "Paroxetine Controlled Release in the Treatment of Menopausal Hot Flashes"; JAMA, Jun. 4, 2003, vol. 289, No. 21; American Medical Associaton.

Roth, et al.; Sertraline Relieves Hot Flashes Secondary to Medical Castration as Treatment of Advanced Prostate Cancer; Psycho-Oncology, 7:129-132 (1998).

Stearns, et al.; A pilot trial assessing the efficacy of paroxetine hydrochloride (Paxil) in controlling hot flashes in breast cancer survivors; Annals of Oncology; 11:17-22 (2000).

Stearns, et al.; "Paroxetine is an effective treatment for hot flashes: results from a prospective randomized clinical trial"; J. Clin Oncol, 23:6919-6930 (Oct. 2005).

Loprinzi, et al.; "Pilot Evaluation of Parooxetine for Treating Hot Flashes in Men"; Mayo Clin Proc. (Oct. 2004) 79(10):1247-1251.

Loprinzi, et al.; "Newer antidepressants inhibit hot flashes"; Menopause, vol. 13, No. 4, pp. 546-548 (2006).

Office Action issued Jun. 2, 2008, in U.S. Appl. No. 11/499,586, 8 pages.

International Search Report issued on Sep. 26, 2008 in application No. PCT/US07/17062.

Harada, "Paroxetine-induced excessive yawning," Psychiatry and Clinical Neurosciences, vol. 60, p. 260, 2006.

Vippagunta et al., "Crystalline solids," Advanced Drug Delivery Reviews, vol. 48, pp. 3-26, 2001.

Gould, "Salt selection for basic drugs," International Journal of Pharmaceutics, vol. 33, pp. 210-217, 1986.

Office Action issued on Aug. 17, 2010 in U.S. Appl. No. 12/292,960 (US 8,658,663).

Office Action issued on Dec. 8, 2010 in U.S. Appl. No. 12/292,960 (US 8,658,663).

Office Action issued on Mar. 1, 2011 in U.S. Appl. No. 12/292,960 (US 8,658,663).

Office Action issued on May 31, 2011 in U.S. Appl. No. 12/292,960 (US 8,658,663).

Notice of Allowance issued on Jan. 8, 2014 in U.S. Appl. No. 12/292,960 (US 8,658,663).

European Search Report issued on Mar. 19, 2014 in application No. EP 13 19 0594.

Loprinzi et al., "Centrally active nonhormonal hot flash therapies," The American Journal of Medicine, vol. 118, No. 128, pp. 1185-1235, 2005.

Curcio et al., "The Potential Role of 5-Hydroxytryptophan for Hot Flash Reduction: A Hypothesis," Alternative Medicine Review, vol. 10, No. 3, pp. 216-221, Sep. 2005.

Notice of Allowance issued on Sep. 2, 2014 in U.S. Appl. No. 14/276,494.

Office Action issued on Jun. 27, 2014 in U.S. Appl. No. 14/276,494.

METHOD OF TREATING THERMOREGULATORY DYSFUNCTION WITH PAROXETINE

CROSS-REFERENCE TO RELATED APPLICATIONS

This application is a continuation of U.S. patent application Ser. No. 12/292,960, filed Dec. 1, 2008 and granted as U.S. Pat. No. 8,658,663 on Feb. 25, 2014, which is a continuation of U.S. patent application Ser. No. 11/499,586 (abandoned), filed Aug. 4, 2006, and priority benefit thereto is claimed under 35 USC §120.

STATEMENT REGARDING FEDERALLY SPONSORED RESEARCH OR DEVELOPMENT

Not Applicable

FIELD OF THE INVENTION

The present invention relates to a method for treating a patient suffering from a thermoregulatory dysfunction, especially hot flashes and flushes associated with hormonal changes due to naturally occurring menopause (whether male or female) or due to chemically or surgically induced menopause. The method is also applicable to treating the hot flashes, hot flushes, or night sweats associated with disease states that disrupt normal hormonal regulation of body temperature. The invention further relates to use of paroxetine or a salt thereof.

BACKGROUND OF THE INVENTION

Hot flashes or flushes are most typically seen in women who are in the process of going through menopause, but are also seen in women who have undergone surgical or chemically induced menopause. They are also seen (less frequently) in men who are undergoing the so-called "male menopause" or who have undergone hormonal ablative therapy. The hot flashes and flushes are connected with a disruption of the hormonal control of thermoregulatory function. In addition, disease states which disrupt the normal hormonal control over thermoregulatory function also result in such hot flashes and flushes.

In the past, the primary treatment for peri- and post-menopausal women having these thermoregulatory dysfunctions have been hormonal replacement therapy primarily because of the known substantial fluctuations in estrogen levels. However, many women, especially those having a history or at higher risk of breast cancer, are reluctant or will not accept hormone replacement therapy. More recently, serotonergic compounds (such as serotonin receptor reuptake inhibitors) and norepinepherine type compounds (particularly norepinepherine uptake inhibitors) have been investigated to some extent for the treatment of hot flashes and flushes in both men and women. Berendsen; *Hypothesis, The role of Serotonin in hot flushes*; Maturitas 36 (2000) 155-164 discusses the role of neurotransmitters, estrogens, and the drugs sertraline and venlafaxine.

US 2006-0100263 relates to combinations of bicifadine and another drug for hot flashes. Paroxetine is one of the "other" drugs mentioned as suitable for the combination therapy. US 2006-0020015 claims the use of combinations of norepinepherine reuptake inhibitors in combination with serotonin reuptake inhibitors. The '015 application also mentions that selective serotonin reuptake inhibitors are being clinically evaluated in hot flashes and particularly mentions that fluoxetine is mentioned in this context in WO 9944601. US 2006-0020014 and US 2004-0130987 have similar disclosures. US 2004-1052710 mentions the use of serotonergic reuptake inhibitors in combination with norepinepherine reuptake inhibitors for the treatment of vasomotor symptoms (the class to which hot flashes and flushes belong) with paroxetine being specifically mentioned as one possible serotonin reuptake inhibitor. US 2002-0042432 (now U.S. Pat. No. 6,369,051) claims the combinations of estrogenic substances with a selective serotonin reuptake inhibitor (SSRI) and paroxetine is specifically mentioned as one of the potential SSRIs for use in the claimed invention.

In addition, sertraline (another SSRI) was found to be effective to some degree in hot flashes as a standalone therapy in Trott, et al *An Open Tial of Sertraline for Menopausal Hot Flushes: Potential Involvement of Serotonin in Vasomotor Instability*; Del. Med. Jrl, September 1997, vol. 69, No. 9, 481-482 and in Roth et al; *SERTRALINE RELIEVES HOT FLASHES SECONDARY TO MEDICAL CASTRATION AS TREATMENT OF ADVANCED PROSTATE CANCER*; Psycho-Oncology 7: 129-132 (1998). U.S. Pat. No. 6,498,184 discusses the role of selective $5\text{-HT}_{2C}$ (a serotonin receptor subtype) agonists for the treatment of hot flushes. US 2004-0092519 relates to use of reboxetine (a selective noradrenaline reuptake inhibitor, i.e. NARI)) for treating hot flaushes. Finally, Stearns et al; *A pilot trial assessing the efficacy of paroxetine hydrochloride (Paxil®) in controlling hot flashes in breast cancer survivors*; Annals of Oncology 11: 17-22, 2000 reports on studies of 10 mg and 20 mg per day dosings of paroxetine hydrochloride monotherapy in women for control of hot flushes.

While the above disclosures mention the use of SSRIs in combinations with other drugs for hot flushes, or paroxetine in particular in combination with other drugs, or even paroxetine as monotherapy for hot flushes, all of these references only mention dosings of paroxetine at 10 mg per day or greater, and generally in the range of 20-50 mg per day. The only exception is U.S. Pat. No. 6,369,051 which mentions a broad dosage range for the SSRI component of the SSRI/estrogenic substance combination, where the SSRI dose is given as 0.1-500 mg/day; preferably 1-200 mg/day, more preferably 20-50 mg/day. However this use is in combination with estrogens. Thus, it can be generally seen that antidepressant therapeutic dosing of the SSRI is typically indicated, or the range is so broad as to effectively not give any real teaching as to a particular dose.

It is generally recognized that at typical antidepressant therapeutic dosing of SSRIs (including paroxetine) there are significant side effects that the patient may not be willing to endure. Women with menopausal hot flashes may not be willing to take antidepressant doses of antidepressant drugs both due to side effects and reluctance to take a treatment for depression. In addition, patients who have multiple other drug treatments, especially cancer therapy treatments or cancer survivors generally do not want to have other medical issues to have to deal with. A simple side effect to most patients who are willing to endure the side effect in other contexts may be overwhelming to those having to deal with multiple drug treatments from other conditions. Thus, there remains a need to obtain relief from the thermoregulatory dysfunction of hot flushes and hot flashes as well as other vasomotor disruptions of thermal regulation while minimizing the side effects and risks associated with the therapeutic agents mentioned above.

Paroxetine is a well characterized molecule in the pharmaceutical and patent literature. Chemical processes for its manufacture are detailed in U.S. Pat. No. 4,861,893; U.S. Pat.

No. 6,172,233; U.S. Pat. No. 6,326,496; U.S. Pat. No. 6,433,179; U.S. Pat. No. 6,541,637 U.S. Pat. No. 6,686,473; U.S. Pat. No. 6,716,985; U.S. Pat. No. 6,881,845; U.S. Pat. No. 6,900,327; and U.S. Pat. No. 6,956,121 to name a few. It is known to exist in various solvate and polymorphic forms include various hydrates, anhydrous forms, isopropanolates, ethanolates, etc, amorphous as well as multiple crystalline forms such as are disclosed in for example, U.S. Pat. No. 4,721,723; U.S. Pat. No. 5,039,803; U.S. Pat. No. 5,672,612; U.S. Pat. No. 5,872,132; U.S. Pat. No. 5,900,423; U.S. Pat. No. 6,080,759; U.S. Pat. No. 6,133,277; U.S. Pat. No. 6,436,956; U.S. Pat. No. 6,440,459; and U.S. Pat. No. 6,638,948, among others. Various pharmaceutical dosage forms are known from the foregoing patents as well as from U.S. Pat. No. 5,955,475; U.S. Pat. No. 6,113,944; U.S. Pat. No. 6,645,523; U.S. Pat. No. 6,660,298; and U.S. Pat. No. 6,699,882 and others for example. Some paroxetine derivatives are disclosed in U.S. Pat. No. 6,063,927. U.S. Pat. No. 6,440,459 and US 2004/0143120 disclose paroxetine maleate and making paroxetine hydrochloride from the maleate. US 2002/0193406; US 2002/0035130; and US 2001/0023253 disclose particularly the mesylate salt, but also many others. US 2002/0090394 discloses controlled release compositions of paroxetine. Paroxetine has also been indicated for a wide range of treatments ranging from its use as an antidepressant (U.S. Pat. No. 4,007,196) to neurologic and mental disorders, (U.S. Pat. No. 5,470,846) to CNS disorders (U.S. Pat. No. 5,985,322) to treatments for nicotine withdrawal, premenstrual symptoms, post-traumatic stress disorder, heroin addiction, etc. Each of the foregoing patent disclosures is incorporated herein (in its entirety) by reference.

OBJECT OF THE INVENTION

It is therefore an object of the invention to provide to a patient suffering from a thermoregulatory dysfunction a dosage form of paroxetine suitable for administration of from 0.1 mg/day to less than an antidepressant effective dosage of paroxetine per day.

Another object of the invention is to provide to a patient suffering from a thermoregulatory dysfunction a dosage form of paroxetine suitable for administration of from 0.1 mg/day to less than 10 mg/day.

Still another object of the invention is to provide to a patient suffering from a thermoregulatory dysfunction a treatment thereof with paroxetine that substantially avoids most and/or substantially reduces the side effects typically obtained from an antidepressant effective amount of paroxetine.

Still further objects of the invention will be apparent to those of ordinary skill.

SUMMARY OF THE INVENTION

The foregoing objects are achieved by providing a method of treating a thermoregulatory dysfunction treatment using paroxetine as free base or a pharmaceutically acceptable salt thereof, in an anhydrate, a hydrate, or solvate form, in any non-crystalline or any crystalline polymorphic form of any of the foregoing in a dosage of from about 0.1 mg/day up to less than an antidepressant therapeutically effective amount of paroxetine.

BRIEF DESCRIPTION OF THE DRAWING

Not Applicable

DETAILED DESCRIPTION OF THE INVENTION

The present invention is a method of treating a thermoregulatory dysfunction treatment using paroxetine as free base or a pharmaceutically acceptable salt thereof, in an anhydrate, a hydrate, or solvate form, in any non-crystalline or any crystalline polymorphic form of any of the foregoing in a dosage of from about 0.1 mg/day up to less than an antidepressant therapeutically effective amount of paroxetine. The invention is also a dosage form of paroxetine in a dose which is less than that effective for its use as an antidepressant.

For the present invention, paroxetine may be in the form of the free base or any pharmaceutically acceptable salt thereof. Pharmaceutically acceptable salts include, but are not limited to, hydohalides (such as hydrochloride, hydrobromide, hydroiodide), sufates (such as sulfate, bisulfate), phosphates (such as mono, di, or tri basic phosphate), oxalate, mesylate, tosylate, pamoate, citrate, carbonate, bicarbonate, maleate, malate, fumarate, as well as many others set forth in the patent references indicated in paragraph 0010 above. Preferably, the paroxetine is present as the free base, the hydrochloride salt, or the mesylate salt or mixtures thereof. Most preferably the paroxetine is present as the hydrochloride salt or the mesylate salt. Paroxetine for use in the present invention may be in the anhydrate, hemihydrate, monohydrate, or higher hydrate forms. Paroxetine for use in the present invention may also be either amorphous or crystalline, the choice being made by the formulator depending upon the formulation and dissolution characteristics desired. Crystalline forms have better stability, but amorphous forms have faster dissolution profiles.

The dosage is about 0.1 mg/day up to less than an antidepressant effective amount of paroxetine (based on the free base, anhydrate); preferably up to about 9.5 mg/day. Preferably the paroxetine can be administered to achieve the invention in amounts of at least 0.5 mg/day, more preferably at least 1 mg/day, still more preferably at least 2 mg/day, even more preferably at least 4 mg/day, up to preferably not more than about 9 mg/day, more preferably not more than about 8.5 mg/day, still more preferably not more than 8 mg/day. Other non-limiting dosages that are specifically suitable for the present invention include 2 mg/day, 2.5 mg/day, 3 mg/day, 3.5 mg/day, 4 mg/day, 4.5 mg/day, 5 mg/day, 5.5 mg/day, 6 mg/day, 6.5 mg/day, 7 mg/day, 7.5 mg/day, 8 mg/day, and 8.5 mg/day.

The present invention is applicable to the treatment of thermoregulatory dysfunction and in particular to such conditions (without limitation) as hot flushes, hot flashes, night sweats, etc. whether or not related to menopause (female or male), perimenopause, hormone ablative therapy (including, but not limited to, anti-estrogenic therapy and antiandrogenic therapy), treatments with other chemical agent or therapeutic agents that are antiestrogenic or antiandrogenic or interfere with thermoregulatory function, surgical procedures (such as, without limitation castration, hysterectomy, ooectomy, etc), and disease states interfering with normal thermoregulatory functioning. Most preferably, the present invention is directed to the treatment of perimenopausal and postmenopausal hot flashes, hot flushes and night sweats in women, whether due to aging, therapeutically induced menopause, or surgically induced menopause. The invention is also preferably directed to hot flashes or hot flushes or night sweats in men whether such symptoms are due to aging, chemical castration, hormonal ablative therapy, or surgical castration.

EXAMPLES

The following non-limiting Examples are presented only to exemplify various embodiments of the invention and do not limit it in any fashion.

Example 1

Females having hot flashes associated with menopause are administered paroxetine (based on free base non-solvate, anhydrate) as follows:

| Form of Paroxetine | Dosage |
|---|---|
| Hydrochloride | 1.0 |
| Hydrochloride | 2.0 |
| Hydrochloride | 3.0 |
| Hydrochloride | 4.0 |
| Hydrochloride | 5.0 |
| Hydrochloride | 6.0 |
| Hydrochloride | 7.0 |
| Hydrochloride | 8.0 |
| Hydrochloride | 9.0 |
| Hydrochloride | 9.5 |
| Mesylate | 1.0 |
| Mesylate | 2.0 |
| Mesylate | 3.0 |
| Mesylate | 4.0 |
| Mesylate | 5.0 |
| Mesylate | 6.0 |
| Mesylate | 7.0 |
| Mesylate | 8.0 |
| Mesylate | 9.0 |
| Mesylate | 9.5 |

After a few days to weeks, the symptoms ameliorate.

Example 2

Females having hot flashes associated with menopause are administered paroxetine (based on free base non-solvate, anhydrate) as follows:

| Form of Paroxetine HCl | Dosage |
|---|---|
| Anhydrous | 1.0 |
| Anhydrous | 2.0 |
| Anhydrous | 3.0 |
| Anhydrous | 4.0 |
| Anhydrous | 5.0 |
| Anhydrous | 6.0 |
| Anhydrous | 7.0 |
| Anhydrous | 8.0 |
| Anhydrous | 9.0 |
| Anhydrous | 9.5 |
| Hemihydrate | 1.0 |
| Hemihydrate | 2.0 |
| Hemihydrate | 3.0 |
| Hemihydrate | 4.0 |
| Hemihydrate | 5.0 |
| Hemihydrate | 6.0 |
| Hemihydrate | 7.0 |
| Hemihydrate | 8.0 |
| Hemihydrate | 9.0 |
| Hemihydrate | 9.5 |
| Monohydrate | 1.0 |
| Monohydrate | 2.0 |
| Monohydrate | 3.0 |
| Monohydrate | 4.0 |
| Monohydrate | 5.0 |
| Monohydrate | 6.0 |
| Monohydrate | 7.0 |
| Monohydrate | 8.0 |
| Monohydrate | 9.0 |
| Monohydrate | 9.5 |

After a few days to weeks, the symptoms ameliorate.

The invention claimed is:

1. A method for treating a patient suffering from a thermoregulatory dysfunction associated with menopause, comprising administering a dosage form of paroxetine to said patient in an amount, based on the paroxetine moiety, of 7.5 mg/day.

2. The method of claim 1, wherein said thermoregulatory dysfunction is a condition selected from the group consisting of hot flashes, hot flushes, night sweats and combinations thereof.

3. The method of claim 1, wherein the dosage form comprises paroxetine free base.

4. The method of claim 1, wherein the dosage form comprises a pharmaceutically acceptable salt of paroxetine.

5. The method of claim 1, wherein the dosage form comprises a pharmaceutically acceptable salt of paroxetine selected from the group consisting of hydrohalides, sulfates phosphates, oxalate, tosylate, pamoate, citrate, carbonate, bicarbonate, maleate, malate, and fumarate.

6. The method of claim 1, wherein the dosage form comprises a pharmaceutically acceptable salt of paroxetine selected from the group consisting of hydrochloride, hydrobromide, and hydroiodide, and combinations of two or more thereof.

7. The method of claim 1, wherein the dosage form comprises a pharmaceuticall acceptable salt of paroxetine selected from the group consisting of sulfate and bisulfate, and combinations thereof.

8. The method of claim 1, wherein the dosage form comprises a pharmaceuticall acceptable salt of paroxetine selected from the group consisting of mono, di, and tri basic phosphates, and combinations of two or more thereof.

9. The method of claim 1, wherein the dosage form comprises paroxetine or a pharmaceutically acceptable salt thereof in anhydrate, hydrate, or solvate form, or combination of two or more thereof.

10. The method of claim 1, wherein the dosage form comprises paroxetine or a pharmaceutically acceptable salt thereof in a crystalline or amorphous form, or a combination thereof.

11. The method of claim 1, wherein the dosage form comprises paroxetine or a pharmaceutically acceptable salt thereof in a crystalline form.

12. The method of claim 1, wherein the dosage form comprises paroxetine or a pharmaceutically acceptable salt thereof in an amorphous form.

* * * * *

UNITED STATES PATENT AND TRADEMARK OFFICE
CERTIFICATE OF CORRECTION

PATENT NO. : 8,946,251 B2  
APPLICATION NO. : 14/157992  
DATED : February 3, 2015  
INVENTOR(S) : Patricia Allison Tewes Richards Page 1 of 1

It is certified that error appears in the above-identified patent and that said Letters Patent is hereby corrected as shown below:

IN THE CLAIMS

Column 6, Claim 5, line 29, please replace "consisting of hydrohalides, sulfates" with -- consisting of hydrohalides, sulfates, --.

Column 6, Claim 7, line 37, please replace "pharmaceticall" with -- pharmaceutically --.

Column 6, Claim 8, line 41, please replace "pharmaceticall" with -- pharmaceutically --.

Column 6, Claim 9, line 46, please replace "combination" with -- combinations --.

Signed and Sealed this
Twenty-fifth Day of August, 2015

Michelle K. Lee
*Director of the United States Patent and Trademark Office*